(12) United States Patent
Chae et al.

(10) Patent No.: US 9,649,388 B2
(45) Date of Patent: May 16, 2017

(54) MAGNETIC NANOPARTICLE-SAMIRNA COMPLEX AND METHOD FOR PREPARING SAME

(71) Applicant: BIONEER CORPORATION, Daejeon (KR)

(72) Inventors: Jeiwook Chae, Daejeon (KR); Hyunjin Chung, Daejeon (KR); Boreum Lee, Gyeonngi-do (KR); Han Oh Park, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 0 days.

(21) Appl. No.: 14/372,211

(22) PCT Filed: Jan. 17, 2013

(86) PCT No.: PCT/KR2013/000360
§ 371 (c)(1),
(2) Date: Jul. 14, 2014

(87) PCT Pub. No.: WO2013/109057
PCT Pub. Date: Jul. 25, 2013

(65) Prior Publication Data
US 2015/0056145 A1 Feb. 26, 2015

(30) Foreign Application Priority Data
Jan. 18, 2012 (KR) .................. 10-2012-0005675

(51) Int. Cl.
| | | |
|---|---|---|
| *A61K 47/48* | (2006.01) | |
| *C12N 15/11* | (2006.01) | |
| *A61K 49/18* | (2006.01) | |
| *A61K 9/14* | (2006.01) | |
| *A61K 31/7105* | (2006.01) | |
| *A61K 9/51* | (2006.01) | |
| *A61K 31/713* | (2006.01) | |
| *A61K 33/24* | (2006.01) | |
| *A61K 9/50* | (2006.01) | |

(52) U.S. Cl.
CPC .......... *A61K 47/48015* (2013.01); *A61K 9/14* (2013.01); *A61K 9/5115* (2013.01); *A61K 31/713* (2013.01); *A61K 31/7105* (2013.01); *A61K 33/24* (2013.01); *A61K 47/48861* (2013.01); *A61K 49/1824* (2013.01); *A61K 49/1857* (2013.01); *C12N 15/11* (2013.01); *A61K 9/5094* (2013.01)

(58) Field of Classification Search
None
See application file for complete search history.

(56) References Cited

U.S. PATENT DOCUMENTS

| | | |
|---|---|---|
| 5,753,263 A | 5/1998 | Lishko et al. |
| 8,697,020 B2 | 4/2014 | Kim et al. |
| 2003/0224353 A1 | 12/2003 | Stein et al. |
| 2006/0078624 A1 | 4/2006 | Zalipsky et al. |
| 2006/0166919 A1 | 7/2006 | Shepard et al. |
| 2007/0135372 A1* | 6/2007 | MacLachlan et al. .......... 514/44 |
| 2008/0227727 A1 | 9/2008 | Erez et al. |
| 2009/0047338 A1 | 2/2009 | Swamy et al. |
| 2011/0206617 A1 | 8/2011 | Roy et al. |
| 2012/0202871 A1 | 8/2012 | Heyes et al. |
| 2014/0248336 A1 | 9/2014 | Stein et al. |
| 2015/0274698 A1 | 10/2015 | Sandanayaka et al. |

FOREIGN PATENT DOCUMENTS

| | | |
|---|---|---|
| KR | 10-2006-0061494 A | 6/2006 |
| KR | 10-2009-0042297 A | 4/2009 |
| KR | 10-2009-0088299 A | 8/2009 |
| WO | 2007021142 A1 | 2/2007 |
| WO | 2007097593 A1 | 8/2007 |
| WO | 2008024983 A2 | 2/2008 |

OTHER PUBLICATIONS

Veiseh et al., Advanced Drug Delivery Reviews 62 (2010) 284-304.*
Bae, K., et al., "Surface functionalized hollow manganese oxide nanoparticles for cancer targeted siRNA delivery and magnetic resonance imaging", "Biomaterials", Jan. 2011, pp. 176-184, vol. 32, No. 1.

(Continued)

*Primary Examiner* — Doug Shultz
(74) *Attorney, Agent, or Firm* — Hultquist, PLLC; Steven J. Hultquist

(57) ABSTRACT

Provided are a SAMiRNA-magnetic nanoparticle complex capable of effectively delivering a double-stranded oligo RNA and magnetic nanoparticles into a cell and a composition capable of simultaneously performing diagnosis and therapy of diseases such as cancer, and the like, containing the same. More specifically, provided is the SAMiRNA-magnetic nanoparticle complex consisting of double-stranded oligo RNA-polymer structures in which a hydrophilic material and a second hydrophobic material are bound to the double-stranded oligo RNA by a simple covalent bond or a linker-mediated covalent bond, and the magnetic nanoparticles in which a first hydrophobic material is bound onto a surface of the magnetic material, as a core.
The SAMiRNA-magnetic nanoparticle complex may have a homogeneous size by a hydrophobic interaction between the first hydrophobic material of the present invention and the second hydrophobic material of the double-stranded oligo RNA structure.
In addition, the hydrophilic material and the second hydrophobic material bound to the double-stranded oligo RNA structure may improve in vivo stability of the double-stranded oligo RNA, an additionally bound ligand may deliver the SAMiRNA-magnetic nanoparticle complex into a target cell even at a relative low concentration of dosage, and the magnetic materials of the magnetic nanoparticles may be used as an imaging agent for diagnosis.

30 Claims, 4 Drawing Sheets

(56) References Cited

OTHER PUBLICATIONS

Czech, M., "MicroRNAs as Therapeutic Targets", "The New England Journal of Medicine", Mar. 16, 2006, pp. 1194-1195, vol. 354, No. 11.

Gary, D., et al., "Polymer-based siRNA delivery: Perspectives on the fundamental and phenomenological distinctions from polymer-based DNA delivery", "Journal of Controlled Release", May 26, 2007, pp. 64-73, vol. 121, No. 1-2.

Kenny, G., et al., "Novel multifunctional nanoparticle mediates siRNA tumour delivery, visualisation and therapeutic tumour reduction in vivo", "Journal of Controlled Release", Oct. 1, 2010, pp. 111-116, vol. 149, No. 2.

Koo, H., et al., "In Vivo Targeted Delivery of Nanoparticles for Theranosis", "Accounts of Chemical Research", Aug. 18, 2011, pp. 1018-1028, vol. 44, No. 10.

Kruetzfeldt, J., et al., "Silencing of microRNAs in vivo with antagomirs", "Nature", Dec. 1, 2005, pp. 685-689, vol. 438.

Lee, J., et al., "All-in-One Target-Cell-Specific Magnetic Nanoparticles for Simultaneous Molecular Imaging and siRNA Delivery", "Angewandte Chemie", Apr. 30, 2009, pp. 4238-4243, vol. 121, No. 23.

Matsuo, T., et al., "Injectable magnetic liposomes as a novel carrier of recombinant human BMP-2 for bone formation in a rat bone-defect model ", "J. Biomed Mater Res A.", Sep. 15, 2003, pp. 747-754, vol. 66, No. 4.

Meister, G., et al., "Sequence-specific inhibition of microRNA- and siRNA-induced RNA silencing", "RNA", Mar. 2004, pp. 544-550, vol. 10, No. 3.

Ryan, B., et al., "Survivin: A new target for anti-cancer therapy", "Cancer Treatment Reviews", Jun. 25, 2009, pp. 553-562, vol. 35, No. 7.

Veiseh, O., et al., "Cell transcytosing poly-arginine coated magnetic nanovector for safe and effective siRNA delivery", "Biomaterials", May 13, 2011, pp. 5717-5725, vol. 32, No. 24.

Veiseh, O., et al., "Chlorotoxin bound magnetic nanovector tailored for cancer cell targeting, imaging, and siRNA delivery", "Biomaterials", Jul. 31, 2010, pp. 8032-8042, vol. 31, No. 31.

Zheng, X., et al., "Preparation and characterization of magnetic cationic liposome in gene delivery", "International Journal of Pharmaceutics", Sep. 20, 2008, pp. 211-217, vol. 366, No. 2009.

Bertrand, J., et al., "Comparison of antisense oligonucleotides and siRNAs in cell culture and in vivo", "Biochemical and Biophysical Research Communications", Aug. 30, 2002, pp. 1000-1004, vol. 296.

Chen, P., et al., "Strand-specific 5'-O-methylation of siRNA duplexes controls guide strand selection and targeting specificity", "RNA", Dec. 19, 2007, pp. 263-274, vol. 14, No. 2.

Jeong, J.H., et al., "siRNA Conjugate Delivery Systems", "Bioconjugate Chem.", Jan. 2009, pp. 5-14, vol. 20, No. 1.

\* cited by examiner

; Double-stranded oligo RNA Structure

; Hydrophobic Material

; Double-stranded oligo RNA

; Hydrophilic Material       ; Magnetic Nanoparticle

; Target-Oriented Ligand      ; First Hydrophobic Material

; Magnetic Nanoparticle Coated with the First Hydrophobic Material

MAGNETIC NANOPARTICLE-SAMIRNA COMPLEX AND METHOD FOR PREPARING SAME

CROSS-REFERENCE TO RELATED APPLICATIONS

This application is a U.S. national phase under the provisions of 35 U.S.C. §371 of International Patent Application No. PCT/KR13/00360 filed Jan. 17, 2013, which in turn claims priority of Korean Patent Application No. 10-2012-0005675 filed Jan. 18, 2012. The disclosures of such international patent application and Korean priority patent application are hereby incorporated herein by reference in their respective entireties, for all purposes.

TECHNICAL FIELD

The present invention relates to a SAMiRNA-magnetic nanoparticles complex containing SAMiRNA which is a nanoparticle consisting of double-stranded oligo RNA structure in which a hydrophilic material and a hydrophobic material are combined with each other so as to improve delivery of the double-stranded oligo RNA effectively used in therapy of cancer, infectious diseases, and the like, and magnetic nanoparticles used in diagnosis, a method of preparing the same, delivery of the double-stranded oligo RNA using the same, and therapy and/or diagnosis technology of diseases including cancer and infection diseases.

BACKGROUND ART

Diagnosis and therapy are two main categories in clinical application of diseases, and recently, a concept of theragnosis which is a technology simultaneously performing diagnosis and therapy utilizing an imaging function in an anti-cancer drug has been introduced. For a successful theragnosis, an imaging agent and a drug are required to be effectively delivered to a target disease area. There are many cases that drug is not delivered as enough to show efficiency of a drug in a target disease area in a drug delivery process, such that an actual effect is not obtained in a clinical therapy, wherein in a serious case, the drug is administered in a body and delivered to a normal tissue rather than the corresponding tissue, thereby causing severe side effect.

In addition, since the diagnosis of the corresponding disease is possible only when an imaging agent is delivered to a target specific area, a method of effectively delivering the drug and the imaging agent to a target area is required (Acc. Chem. Res., 2011, 44 (10), pp 1018-1028).

As the imaging modality, fluorescence optical imaging, magnetic resonance imaging (MRI), positron-emission tomography (PET) and computed tomography (CT), and the like, have been utilized. The imaging agent used in the imaging modality equipment has been variously developed. In particular, in view of diagnosis and therapy of the disease, a magnetic nanoparticle has advantages of being non-toxic, having excellent biocompatibility, being injected through blood vessel, and being accumulated in a high content in human tissue (Taeeok Kim, nano-biotechnology, Biotech Policy Research Center, 2009).

The magnetic nanoparticles in a nano-bio field have been used in wide range of applications such as separation of biological materials, magnetic resonance imaging diagnosis imaging agent, a biosensor including a giant magneto resistive sensor, drug/gene delivery, magnetic therapy at high-temperature, and the like. Specifically, the magnetic nanoparticle may be used as an imaging agent for diagnosing a molecular magnetic resonance imaging. The magnetic nanoparticles shorten a spin-spin relaxation time of the hydrogen atoms of water molecules around the nanoparticles to amplify MRI signal, which is widely and currently used in resonance imaging diagnosis.

In addition, the magnetic nanoparticle may also be used in therapy in vivo through delivery of drug or gene. The drug or the gene is loaded on the magnetic nanoparticle by chemical bond or absorption and moved to a desired position by an external magnetic field, and the drug and the gene are discharged to a specific area to bring selective therapy effect (see Korean Patent Publication No 0819378). Currently, as a mean of delivering the drug using the magnetic nanoparticle, magnetic liposome has emerged as the most powerful tool. The magnetic liposome has a form in which magnetic nanoparticles are contained in liposome surrounded with phospholipid layers and contains the drug, the gene, and the like, in the liposome, to be delivered to a specific area (Toshihiro Matsuo et al., J. Biomedical Materials Research Part A, 66A(4): 747-754, 2003). In addition, the magnetic nanoparticles may have a function of tracking a specific tissue by chemical therapy of the surface of liposome. Recently, a magnetic cationic liposome (MCL) increasing adsorption and accumulation properties in a biotissue was developed in order that the magnetic liposome effectively tracks cancer cell (XiaoliZheng et al., International J. Pharmaceutics, 366:211-217, 2009). However, a stable magnetic nanoparticles having improved biocompatibility and stability is still required.

In addition, when the nanoparticles are injected in vivo, long circulating property in which the nanoparticles are well-dispersed and circulated for an appropriate time without agglomeration in blood is required. However, since the nanoparticle has a large surface area, the nanoparticles are well-agglomerated due to a biofouling phenomenon that various plasma protein, salts, and the like, are well attached to the nanoparticles, to thereby be easily removed by reticuloendothelial cells (reticuloendothelial system: RES) such as Kuffer cell of liver, macrophage of spleen. Therefore, within several minutes after injecting the nanoparticles into the body, the nanoparticles disappear in blood and may not reach to the desired tissue. In addition, when iron oxide nanoparticles are not sufficiently stabilized in vivo, the original structure thereof is changed, such that magnetic property may be changed or biodegradation may rapidly occur. Therefore, a technology of coating a surface of a nanoparticle using polymer such as polyethylene glycol (PEG) to increase biocompatibility and stability has been studied (Polymer Science and Technology. Vol 19 (2). 2008. 116-124).

Meanwhile, it was found that siRNA has remarkable effect in inhibiting expression of a specific gene in an animal cell, and thus, is being focused as a gene therapeutic agent, and due to high activity and precise gene selectivity thereof, siRNA is expected to be an alternative therapeutic agent to antisense oligonucleotide (ODN) currently being used as a therapeutic agent as a result of the past 20-year's research (Dana J. Gary et al. Journal of Controlled Release 121:64-73, 2007).

In particular, siRNA techniques used with the therapeutic purpose has a large advantage of being easily designed as compared to other medical products and effectively inhibiting expression of a specific gene, and high target selectivity and the gene expression inhibition by RNAi of siRNA, and the like, uses mechanism naturally present in vivo to have low toxicity. In addition, the nanoparticle in which a material capable of binding to receptor present in a specific area is bound with drug capable of killing cancer cell, and the like, may deliver the drug with the specific cell as a target.

The biggest challenge which is required to be overcome in treating diseases such as cancer, and the like, is to develop a technology of selecting an appropriate 'target material (targeting agent)' capable of precisely and selectively delivering the nanoparticles containing therapeutic agent to a target tissue of cancer cell, and the like, and binding the target material to the nanoparticles. The target material or ligand bound to the nanoparticles needs to be bound to a surface of tumor cell by an appropriate method to operate the receptor, thereby enabling endocytosis the anticancer agent contained in the nanoparticles in cells (Junung, Lee, nanoparticles and target tracking system for cancer therapy, a high-tech information analysis report, Korea Institute of Science and Technology Information, 2004).

Recently, in order to improve an intracellular delivery efficiency of siRNA, technology of using a siRNA conjugate in which hydrophilic material which is a biocompatible polymer (for example, polyethylene glycol (PEG) is bound to the siRNA by a simple covalent bond or a linker-mediated covalent bond, to thereby secure stability of siRNA and have effective cell membrane penetrability was developed (see Korean Patent Publication No. 883471). However, the conjugation (PEGylation) of the polyethylene glycol (PEG) to the siRNA still has disadvantages in that stability is low in vivo and delivery to the target tissue is not smooth.

In order to solve the problem, a double-stranded oligo RNA structure in which the hydrophilic material and the hydrophobic material are bound to the double-stranded oligo RNA was developed, the double-stranded oligo RNA structure forms self-assembling nanoparticles by a hydrophobic interaction of the hydrophobic material. The self-assembling nanoparticle is referred to as 'SAMiRNA' (Korean Patent Laid-Open Publication No. 2009-0042297).

SUMMARY OF PRESENT INVENTION

An object of the present invention is to provide a SAMiRNA which is a nanoparticle consisting of double-stranded oligo RNA structure in which a hydrophilic material and a hydrophobic material are bound to a double-stranded oligo RNA used for therapy, a SAMiRNA-magnetic nanoparticle complex consisting of magnetic nanoparticles used for diagnosis, and a method of preparing the same. A delivery capacity to a desired target may be enhanced by additionally bonding a target-specific ligand to the hydrophilic material of the double-stranded oligo RNA structure in the present invention. The SAMiRNA-magnetic nanoparticle complex may be formed by an interaction between the hydrophobic material in the SAMiRNA and the hydrophobic material coated onto a surface of the magnetic materials of the magnetic nanoparticles.

In addition, another object of the present invention is to provide a composition for therapy and/or diagnosis, containing the SAMiRNA-magnetic nanoparticle complex, and a method of treating and/or diagnosing diseases using the same, wherein the SAMiRNA-magnetic nanoparticle complex according to the present invention may be significantly useful in therapy and/or diagnosis of various diseases including cancer and infectious diseases.

Further, in the SAMiRNA-magnetic nanoparticle complex, a SAMiRNA forming technology may be applied to a single-stranded oligonucleotide, in particular, a single-stranded antisense oligonucleotide (ASO) with therapeutic purpose, as well as the double-stranded oligo RNA.

The SAMiRNA-magnetic nanoparticle complex may increase a cell delivery efficiency due to improved in vivo stability of the double-stranded oligo RNA and a homogeneous size of the nanoparticle to have excellent therapeutic efficacy, and may be utilized with a diagnosis purpose due to property of the magnetic nanoparticle. That is, the SAMiRNA-magnetic nanoparticle complex is capable of being used in a so-called theragnosis in which therapy and diagnosis are simultaneously performed, to thereby be significantly useful throughout various industrial fields such as basic research for biotechnology, pharmaceutical industry, and the like, as a new type of double-stranded oligo RNA delivery system for diagnosis and therapy of diseases.

In addition, the double-stranded oligo RNA for therapy may be efficiently delivered into a target cell including cancer through a target cell-specific delivery using the additionally bound ligand, such that diagnosis of cancer and therapy through the delivered double-stranded oligo RNA may be simultaneously performed. The SAMiRNA-magnetic nanoparticle complex containing the ligand bound thereto may inhibit a non-specific delivery to other organs and cells to effectively and specifically perform the diagnosis and the therapy of cancer.

In particular, when the complex consists of the magnetic nanoparticles and the double-stranded oligo RNA structure in order to improve the delivery of the magnetic nanoparticles in vivo, the magnetic nanoparticles may be endocytosed in the SAMiRNA to form a more uniform SAMiRNA-magnetic nanoparticle complex. The SAMiRNA-magnetic nanoparticle complex is used to deliver the double-stranded oligo RNA in a cancer-specific way, such that an activity of the double-stranded oligo RNA may be exhibited in the target tissue even at a relatively low concentration of dosage.

DESCRIPTION OF DRAWINGS

(A) an electron micrograph of the magnetic nanoparticle, and (B) a transmission micrograph of the SAMiRNA-magnetic nanoparticle complex.

(A) Non-administered Group, and (B) SAMiRNA-magnetic nanoparticle complex-administered Group. (imaging signal of the cancer tissue in MRI is shown as a black color, scanning angle—Coronal Section, coronal section Axial Section, section perpendicular to the side)

BEST MODE

Hereinafter, the present invention will be described in more detail.

In order to provide a new theragnosis technology in which diagnosis and therapy of diseases such as cancer, and the like, are simultaneously performed, the present invention provides a SAMiRNA-magnetic nanoparticle complex consisting of magnetic nanoparticles having a structure in which a first hydrophobic material is coated onto a surface of magnetic materials and SAMiRNA including a double-stranded oligo RNA structure in which a hydrophilic material and a second hydrophobic material are bound to a double-stranded oligo RNA.

Term 'first hydrophobic material' of the present invention means a hydrophobic material coated onto the surface of the magnetic material of the magnetic nanoparticle, and term 'second hydrophobic material' means a hydrophobic material contained in the double-stranded oligo RNA structure of SAMiRNA by being connected to each other with a covalent bond. The first hydrophobic material and the second hydrophobic material may be the same as or similar to each other or may be different from each other, which will be described in more detail.

Figure 1:
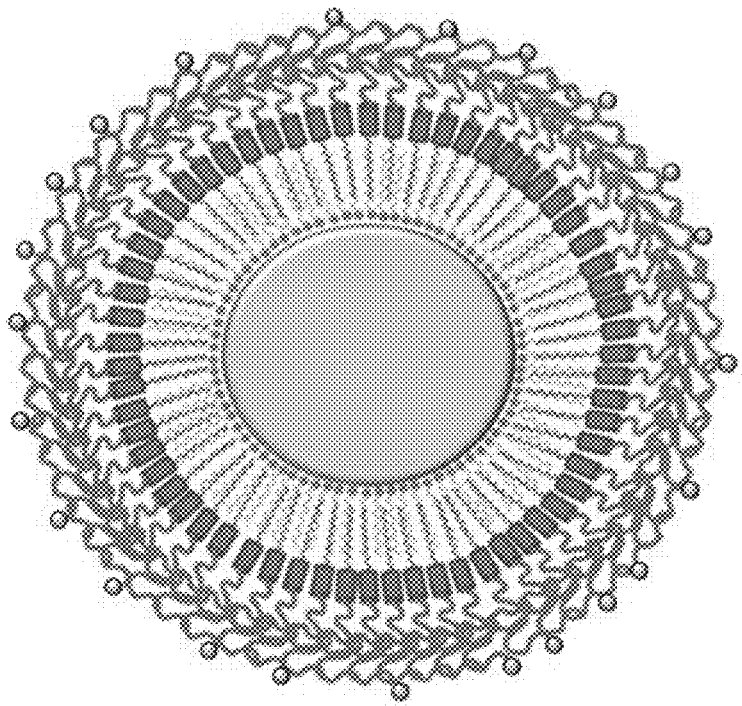
FIG. 1 is a schematic view of a SAMiRNA-magnetic nanoparticle complex.
Figure 1:
Figure 1:
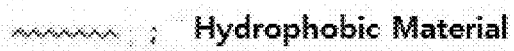
Figure 1:
Figure 1:
Figure 1:
Figure 1:
Figure 1:
Figure 1:
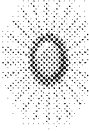

The SAMiRNA-magnetic nanoparticle complex provided in the present invention has a structure in which the magnetic nanoparticles in which the first hydrophobic material is coated onto the surface of the magnetic material are positioned as a core in the innermost side thereof, a hydrophobic interaction is formed between the first hydrophobic material coated onto the surface of the magnetic materials and the second hydrophobic material contained in the double-stranded oligo RNA structure (the second hydrophobic material is bound to the double-stranded oligo RNA), and the hydrophilic material is bound to the outermost side of the double-stranded oligo RNA which is an opposite direction to the double-stranded oligo RNA (see FIG. 1). Term 'coating' of the present invention means all cases of physical adsorption or chemical bond of the first hydrophobic material onto the magnetic material.

In addition, the bond between the hydrophilic material and the hydrophobic material in the SAMiRNA and the double-stranded oligo RNA contained in the SAMiRNA-magnetic nanoparticle complex is preferably a covalent bond, but is not necessarily limited thereto.

The magnetic nanoparticles of the SAMiRNA-magnetic nanoparticle complex contain the magnetic materials to be significantly useful for a diagnosis method using magnetic property. Specifically, the magnetic nanoparticles may be applied to various diagnosis methods including magnetic resonance imaging (MRI) diagnosis method using magnetic property.

The magnetic material of the magnetic nanoparticles may be limitlessly used as long as it is a particle having a diameter of 1 nm to 200 nm, preferably, 2 nm to 100 nm and may be a magnetic metal or a magnetic metal oxide.

More specifically, the magnetic metal may be preferably made of one or more metals selected from the group consisting of iron family metal elements (Fe, Ni, Co), rare earth elements (La, Ce, Pr, Nd, Pm, Sm, Gd, Tb, Dy, Ho, Er, Tm, Yb, Lu), coinage metal elements (Cu, Ag, Au), zinc group elements (Zn, Cd, Hg), aluminum group elements (Al, Ga, In, Tl), alkaline earth metal elements (Ca, Sr, Ba, Ra), and platinum group elements (Pt, Pd, and the like), or alloys thereof.

The magnetic metal oxide may be preferably made oxide of one or more metals selected from the group consisting of iron family metals (Fe, Ni, Co), rare earth elements (La, Ce, Pr, Nd, Pm, Sm, Eu, Gd, Tb, Dy, Ho, Er, Tm, Yb, Lu), coinage metal elements (Cu, Ag, Au), zinc group elements (Zn, Cd, Hg), aluminum group elements (Al, Ga, In, Tl), alkaline earth metal elements (Ca, Sr, Ba, Ra), and platinum group elements (Pt, Pd, and the like), or alloys thereof.

The first hydrophobic material coated onto the surface of the magnetic material may be limitlessly used as long as a material may form the SAMiRNA-magnetic nanoparticle complex of the present invention, and as a non-limited example thereof, may preferably include $C_6$ to $C_{25}$ aromatic compound, $C_6$ to $C_{25}$ ether, $C_6$ to $C_{25}$ aliphatic hydrocarbons and $C_6$ to $C_{25}$ amines, and when considering formation of the nanoparticle complex, saturated or unsaturated fatty acids and/or alkyl amines may be preferably used.

The double-stranded oligo RNA structure configuring the SAMiRNA in the present invention has a structure represented by the following Formula (1):

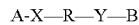   Formula (1)

in the Formula (1) above, one of A and B is a hydrophilic material, the other one is a second hydrophobic material, R is a double-stranded oligo RNA; and X and Y are preferably a simple covalent bond or a linker-mediated covalent bond, but the present invention is not limited thereto.

In particular, the double-stranded oligo RNA structure configuring the SAMiRNA in the present invention has preferably a structure represented by the following Formula (1'):

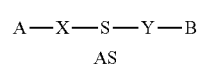   Formula (1')

in the Formula (1') above, one of A and B is a hydrophilic material, the other one is a second hydrophobic material, X and Y are each a simple covalent bond or a linker-mediated covalent bond independently of each other, S is a sense strand of the double-stranded oligo RNA, and AS is an antisense strand of the double-stranded oligo RNA.

In addition, a delivery capacity to a desired target may be enhanced by additionally bonding a target-specific ligand to the hydrophilic material of the double-stranded oligo RNA structure configuring the SAMiRNA of the present invention.

The ligand in the present invention means all materials of specifically binding to the receptor increasing target cell internalization through receptor-mediated endocytosis (RME), and in particular, may be selected from the group consisting of target specific antibody, aptamer, peptide or a receptor-specific chemical material, which is bound in a target-specific way to function receptor-mediated endocytosis (RME), but the present invention is not limited thereto. In addition, the receptor-specific chemical material is preferably selected from the group consisting of folate, N-acetyl galactosamine (NAG) and mannose, but the present invention is not limited thereto.

In order to bind the materials such as the ligand, and the like, the hydrophilic material of the double-stranded oligo RNA structure may be modified so as to have functional groups required for bonding to the materials such as the ligand, and the like. Among the hydrophilic materials, in particular, polyethylene glycol (PEG) is significantly appropriate for preparing the double-stranded oligo RNA structure of the present invention since various molecular weights and functional groups may be introduced thereinto, affinity in vivo is excellent, an immune stimulation is not induced, that is, bio-compatibility is excellent, in vivo stability of the double-stranded oligo RNA is increased, and a delivery efficiency is increased.

In the double-stranded oligo RNA structure of the present invention, the double-stranded oligo RNA preferably consists of 19 to 31 nucleotides. As the double-stranded oligo RNA usable in the present invention, a double-stranded oligo RNA derived from any gene used for gene therapy or gene research or having a possibility to be used for gene therapy or gene research, that is, capable of sequence-specifically binding to the gene may be adopted.

The covalent bond may be any one of a non-degradable bond or a degradable bond. Here, examples of the non-degradable bond may include an amide bond or a phosphate bond, and examples of the degradable bond may include a disulfide bond, an acid degradable bond, an ester bond, an anhydride bond, a biodegradable bond or an enzymatically degradable bond, and the like, but the present invention is not necessarily limited thereto.

The second hydrophobic material may be limitlessly used as long as the SAMiRNA-magnetic nanoparticle complex of the present invention may be formed, and preferably have a molecular weight of 100 to 2,000. In particular, the second hydrophobic material may include a steroid derivative, a glyceride derivative, glycerol ether, polypropylene glycol, unsaturated or saturated $C_{12}$ to $C_{50}$ hydrocarbons, diacylphosphatidylcholine, fatty acid, phospholipid, lipopolyamine, and the like, as an example; but is not limited thereto. It is apparent to those skilled in the art that any second hydrophobic material is capable of being used as long as a material is to meet objects of the present invention.

In particular, the steroid derivative may be selected from the group consisting of cholesterol, cholestanol, cholic acid, cholesteryl formate, cholestanyl formate, and cholestanyl amine, and the glyceride derivative may be selected from the group consisting of mono-, di- and tri-glyceride, and the like, wherein a fatty acid of the glyceride is unsaturated or saturated $C_{12}$ to $C_{50}$ fatty acid.

The second hydrophobic material generates a hydrophobic interaction with the first hydrophobic material, wherein the hydrophobic interaction serves to form the SAMiRNA-magnetic nanoparticle complex consisting of the magnetic nanoparticles and the double-stranded oligo RNA structure, and the first hydrophobic material and the second hydrophobic material may be the same as each other or different from each other.

In addition, the hydrophilic material is preferably derived from a non-ionic polymer having a molecular weight of 1,000 to 10,000. For example, the non-ionic hydrophilic materials such as polyethylene glycol (PEG), polyvinylpyrolidone, polyoxazoline, and the like, may be preferably used, but the present invention is not necessarily limited thereto.

As described above, the double-stranded oligo RNA structure of the present invention has a structure in which the hydrophilic material and the second hydrophobic material are bound to both ends of the double-stranded oligo RNA, and as an example thereof, the double-stranded oligo RNA structure in which the second hydrophobic material is bound to 5' end of the sense strand of the double-stranded oligo RNA and the hydrophilic material is bound to 3' end thereof as shown in the following Formula (2) may be used:

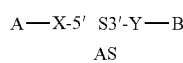

Formula (2)

In the Formula (2) above, A is a second hydrophobic material, B is a hydrophilic material, S is a sense strand of the double-stranded oligo RNA, AS is an antisense strand of the double-stranded oligo RNA, and X and Y are preferably and each a simple covalent bond or a linker-mediated covalent bond independently of each other, but the present invention is not limited thereto.

A method of preparing the double-stranded oligo RNA structure represented by the Formula (2) above may include:

(1) synthesizing an RNA single strand based on a solid support containing a hydrophilic material bound thereto, preferably, CPG;

(2) covalently binding the second hydrophobic material to 5' end of the RNA single strand;

(3) separating the RNA-polymer structure from the solid support (CPG) when the synthesis is completed; and (4) preparing the double-stranded oligo RNA structure by annealing the prepared RNA-polymer structure and a separately synthesized RNA single strand of a complementary sequence thereto.

After the step (3) or (4) above, when the preparation is completed, the reactant may be purified by high performance liquid chromatography (HPLC) and a molecular weight thereof may be measured by MALDI-TOF mass spectrometry to confirm whether or not a desired double-stranded oligo RNA and a double-stranded oligo RNA structure are prepared.

In the preparation method, the synthesizing of the RNA single strand of a complementary sequence to a sequence of the RNA single strand synthesized in the step (1), which is an independent synthesis process, may be performed before the step (1) or may be performed during any one step of the steps (1) to (4). In addition, the RNA single strand of a complementary sequence to the RNA single strand synthesized in the step (1) may contain a phosphate group bound to 5' end thereof.

In another exemplary embodiment, a double-stranded oligo RNA structure in which a hydrophilic material is bound to 5' end of the sense strand of the double-stranded oligo RNA and a second hydrophobic material is bound to 3' end thereof as shown in the following Formula (3) may be used:

Formula (3)

in the Formula (3) above, A is a second hydrophobic material, B is a hydrophilic material, S is a sense strand of the double-stranded oligo RNA, AS is an antisense strand of the double-stranded oligo RNA, and X and Y are preferably a simple covalent bond or a linker-mediated covalent bond, but the present invention is not limited thereto.

A method of preparing the double-stranded oligo RNA structure represented by the Formula (3) above may include:

(1') synthesizing an RNA single strand based on a solid support containing a functional group bound thereto, preferably, CPG;

(2') covalently binding a hydrophilic material to 5' end of the RNA single strand to be synthesized;

(3') separating an RNA-hydrophilic polymer structure containing the functional group bound thereto from the solid support (CPG) when the synthesis is completed;

(4') binding a second hydrophobic material to the RNA-hydrophilic polymer structure through the functional group to synthesize an RNA-polymer structure in which the hydrophilic material and the second hydrophobic material are bound to both ends of the RNA; and (5') preparing the double-stranded oligo RNA structure by annealing the prepared RNA-polymer structure and a separately synthesized RNA single strand of a complementary sequence thereto.

After the step (4') or (5') above, when the preparation is completed, the reactant may be purified by high performance liquid chromatography (HPLC) and a molecular weight thereof may be measured by MALDI-TOF mass spectrometry to confirm whether or not a desired double-stranded oligo RNA and a double-stranded oligo RNA structure are prepared. In the preparation method, the synthesizing of the RNA single strand of a complementary sequence to a sequence of the RNA single strand synthesized in the step (1'), which is an independent synthesis process, may be performed before the step (1') or may be performed during any one step of the steps (1') to (5'). In addition, the RNA single strand of a complementary sequence to the RNA single strand synthesized in the step (1') may contain a phosphate group bound to 5' end thereof.

In addition, in a double-stranded oligo RNA structure containing a ligand bound thereto, the ligand may be bound to the hydrophilic material of the double-stranded oligo RNA structure. As an example thereof, the double-stranded oligo RNA structure in which the hydrophilic material is bound to 3' end of the sense strand of the double-stranded oligo RNA, the ligand is bound to the hydrophilic material, and the second hydrophobic material is bound to 5' end thereof in the following Formula (4) may be used:

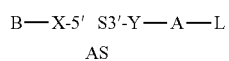

Formula (4)

in the Formula (4) above, A is a hydrophilic material, B is a second hydrophobic material, S is a sense strand of the double-stranded oligo RNA, AS is an antisense strand of the double-stranded oligo RNA, X and Y are preferably a simple covalent bond or a linker-mediated covalent bond, but the present invention is not limited thereto, and L is a ligand specifically binding to a receptor promoting internalization of a target cell, through receptor-mediated endocytosis (RME).

A method of preparing the double-stranded oligo RNA structure containing the ligand bound thereto represented by the Formula (4) above may include:

(1") binding a hydrophilic material to a solid support (CPG) containing a functional group bound thereto;

(2") synthesizing an RNA single strand based on the solid support (CPG) containing a functional group-hydrophilic material bound thereto;

(3") covalently binding the second hydrophobic material to 5' end of the RNA single strand to be synthesized;

(4") separating a functional group-RNA-polymer structure from the solid support (CPG) when the synthesis is completed;

(5") preparing an RNA-polymer structure containing a ligand bound to an end of the hydrophilic material using the functional group; and (6") preparing the double-stranded oligo RNA structure by annealing the prepared RNA-polymer structure containing the ligand bound thereto and an RNA single strand of a complementary sequence thereto.

After the step (4"), (5") or (6") above, when the preparation is completed, the reactants, the RNA-polymer structure, and the RNA single strand of a complementary sequence thereto may be separated and purified by high performance liquid chromatography (HPLC) and molecular weights thereof may be measured by MALDI-TOF mass spectrometry to confirm whether or not a desired double-stranded oligo RNA and a double-stranded oligo RNA structure are prepared.

In the preparation method, the synthesizing of the RNA single strand of a complementary sequence to a sequence of the RNA single strand synthesized in the step (3"), which is an independent synthesis process, may be performed before the step (1") or may be performed during any one step of the steps (1") to (6").

In another exemplary embodiment, a double-stranded oligo RNA structure in which the hydrophilic material or the second hydrophobic material is bound to 5' end of the sense strand and the antisense strand of the double-stranded oligo RNA and the ligand is bound thereto as shown in the following Formula (5) may be used:

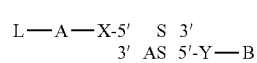

Formula (5)

in the Formula (5) above, A is a hydrophilic material, B is a second hydrophobic material, S is a sense strand of the double-stranded oligo RNA, AS is an antisense strand of the double-stranded oligo RNA, X and Y are preferably a simple covalent bond or a linker-mediated covalent bond, but the present invention is not limited thereto, and L is a ligand specifically binding to a receptor promoting internalization of a target cell, through receptor-mediated endocytosis (RME).

A method of preparing the double-stranded oligo RNA structure containing the ligand bound thereto represented by the Formula (5) above may include:

(1''') synthesizing an RNA single strand based on a solid support;

(2''') covalently binding a hydrophilic material to 5' end of the RNA single strand;

(3''') separating an RNA-hydrophilic polymer structure containing the ligand bound thereto and a single strand of a separately synthesized RNA-second hydrophobic polymer structure of a complementary sequence thereto from the solid support; and (4''') preparing the double-stranded oligo RNA structure containing the ligand bound thereto by annealing the RNA-hydrophilic polymer structure and the RNA-second hydrophobic polymer structure of a complementary sequence thereto.

After the step (3''') or (4''') above, when the preparation is completed, the reactant may be purified by high performance liquid chromatography (HPLC) and a molecular weight thereof may be measured by MALDI-TOF mass spectrometry to confirm whether or not a desired double-stranded oligo RNA containing the ligand bound thereto and a double-stranded oligo RNA structure are prepared.

In the preparation method, the synthesizing of the RNA-second hydrophobic polymer structure of a complementary sequence to a sequence of the RNA single strand synthesized in the step (1'''), which is an independent synthesis process, may include: synthesizing an RNA single strand of a complementary sequence to the RNA single strand of the step (1''') before the step (1''') or during any one step of the steps (1''') to (4'''), covalently binding the second hydrophobic material to synthesize a single strand of an RNA-second hydrophobic polymer structure containing the second hydrophobic material bound thereto, and separating the synthesized single strand from the solid support.

The functional group of the hydrophilic material may be substituted with other functional groups as needed. Among the hydrophilic materials, in particular, polyethylene glycol (PEG) is significantly appropriate for preparing the double-stranded oligo RNA structure of the present invention since the PEG has an end of introducing various molecular weights and functional groups thereinto and excellent affinity in vivo, does not induce an immune stimulation, and improves solubility to water to increase gene delivery efficiency in vivo.

In another exemplary embodiment, a double-stranded oligo RNA structure in which a hydrophilic material is bound to 5' end of the double-stranded oligo RNA sense strand, the ligand is bound to the hydrophilic material, and a second hydrophobic material is bound to 3' end thereof as shown in the following Formula (6) may be used:

Formula (6)

in the Formula (6) above, A is a hydrophilic material, B is a second hydrophobic material, S is a sense strand of the double-stranded oligo RNA, AS is an antisense strand of the double-stranded oligo RNA, X and Y are preferably a simple covalent bond or a linker-mediated covalent bond, but the present invention is not limited thereto, and L is a ligand specifically binding to a receptor promoting internalization of a target cell, through receptor-mediated endocytosis (RME).

A method of preparing the double-stranded oligo RNA structure containing the ligand bound thereto represented by the Formula (6) above may include:

(1'''') synthesizing an RNA single strand based on a solid support (CPG) containing a functional group bound thereto;

(2'''') covalently binding a hydrophilic material to 5' end of the RNA single strand to be synthesized;

(3'''') synthesizing a functional group-RNA-hydrophilic polymer structure containing the ligand bound to the hydrophilic material of the RNA single strand;

(4'''') separating the functional group-RNA-hydrophilic polymer structure containing the ligand bound thereto from the solid support (CPG) when the synthesis is completed;

(5'''') binding a second hydrophobic material to the functional group-RNA-hydrophilic polymer structure through the functional group to synthesize an RNA-polymer structure containing the ligand bound thereto; and (6'''') preparing the double-stranded oligo RNA structure by annealing the prepared RNA-polymer structure containing the ligand bound thereto and a separately synthesized RNA single strand of a complementary sequence thereto.

After the step (5'''') or (6'''') above, when the preparation is completed, the reactant may be purified by high performance liquid chromatography (HPLC) and a molecular weight thereof may be measured by MALDI-TOF mass spectrometry to confirm whether or not a desired double-stranded oligo RNA containing the ligand bound thereto and a double-stranded oligo RNA structure are prepared. In the preparation method, the synthesizing of the RNA single strand of a complementary sequence to a sequence of the RNA single strand synthesized in the step (1), which is an independent synthesis process, may be performed before the step (1'''') or may be performed during any one step of the steps (1'''') to (6'''').

In addition, the method of preparing the SAMiRNA-magnetic nanoparticle complex according to the present invention may include:

(a) preparing a double-stranded oligo RNA structure containing a hydrophilic material and a second hydrophobic material bound thereto;

(b) preparing a magnetic nanoparticle containing a first hydrophobic material coated on a surface of the magnetic material; and (c) mixing a SAMiRNA consisting of the double-stranded oligo RNA structure prepared in the steps (a) and (b) above and the magnetic nanoparticle containing the first hydrophobic material coated on the surface of the magnetic material with each other.

In the preparation method above, the step (a) and the step (b) above do not have to be sequentially performed, such that the steps (a) and (b) may be performed regardless of the order. That is, the step (b) may be performed before the step (a). In addition, the double-stranded oligo RNA structure prepared in the step (a) may further contain a ligand.

A mass ratio between the magnetic nanoparticles and the SAMiRNA in the SAMiRNA-magnetic nanoparticle complex is preferably 0.01:1 to 100:1, and more preferably, 0.1:1 to 10:1.

It is preferred that the SAMiRNA-magnetic nanoparticle complex has a size of 50 to 300 nm, and has polydispersity index (PDI) of 0.01 to 0.4, and more preferably, 0.1 to 0.3.

In addition, in the SAMiRNA-magnetic nanoparticle complex, a SAMiRNA forming technology may be applied to a single-stranded oligonucleotide, in particular, a single-stranded antisense oligonucleotide (ASO) with therapeutic purpose, as well as the double-stranded oligo RNA. That is, in the double-stranded oligo RNA structure configuring the SAMiRNA, the single-stranded oligonucleotide structure containing a single-stranded antisense oligonucleotide (ASO) rather than a double-stranded oligonucleotide may be used to form a complex with the magnetic nanoparticles.

The ASO technology is a technology of adjusting information delivery from gene to protein by degrading mRNA through a single-stranded RNA or DNA strand. That is, base sequences hybridized sufficiently in a complimentary and specific way are selected to desirably inhibit expression of the target protein. The ASO is sequence-specifically bound to a target gene, thereby not having an effect on expression of other genes rather than the target gene. Therefore, the ASO technology is a tool useful for analysis of functions in vivo of the specific protein, and has a possibility of being utilized as a gene therapy with respect to specific diseases (*FASEBJ*. 9, 1288-1296, 1995). In particular, an antagomir which is one of new kinds of the single-stranded antisense oligonucleotide has been recently developed to be used in inhibiting functions of microRNA derived in cells. It is known that the antagomir which is a chemically synthesized and short RNA, or a micro RNA inhibitor is complimentarily bound to the microRNA which is a target to inhibit the functions thereof. In general, it is preferred that the antagomir has a chemically modified structure such as 2' methoxy, phosphothioate, or the like, in order to prevent the antagomir from being degraded. In this regard, the antagomir inhibiting the functions of miRNA related with various diseases including cancer, heart and lung fibrosis has been currently reported ("Silencing of microRNAs in vivo with 'antagomirs' Nature, December 2005, 438(7068): 685-689; "MicroRNAs as Therapeutic Targets" New England J. Medicine, 2006, 354 (11): 1194-1195; Meister G. et al., "Sequence-specific inhibition of microRNA- and siRNA-induced RNA silencing" RNA, March 2004, 10 (3): 544-550).

The single-stranded antisense oligonucleotide (ASO) in the present invention means all single-stranded oligonucleotides having a function of inhibiting expression or activity of specific genes including antagomir as well as conventional antisense.

In particular, the single-stranded oligonucleotide structure according to the present invention has a structure represented by the following Formula (7):

A-X-ASO-Y—B    Formula (7)

in the Formula (7) above, one of A and B is a hydrophilic material, the other one is a second hydrophobic material, ASO is a single-stranded antisense oligonucleotide; and X and Y are preferably and each a simple covalent bond or a linker-mediated covalent bond independently of each other, but the present invention is not limited thereto.

The hydrophilic material, the second hydrophobic material, and the simple covalent bond or the linker-mediated covalent bond represented by X and Y in the Formula (7) above have properties as defined in the above-described SAMiRNA structure using the double-stranded oligo RNA.

In the present invention, it is preferred that the ASO includes 10 to 50 oligonucleotides, and more preferably, 13 to 25 oligonucleotides.

In addition, in order to improve in vivo stability, the ASO includes oligodeoxynucleotide (ODN) with various modifications having resistance to nucleolytic enzymes. The modification may be one or more combinations selected from modification in which —OH group at: 2' carbon in a sugar structure in one or more nucleotides is substituted with —CH$_3$(methyl), —OCH$_3$, —N$_2$, —F(fluorine), —O-2-methoxyethyl, —O-propyl, —O-2-methylthioethyl, —O-3-aminopropyl, —O-3-dimethylaminopropyl, —O—N-methylacetamido or —O-dimethylamidooxyethyl; modification in which oxygen in a sugar structure in nucleotides is substituted with sulfur; and modification to phosphorothioate or boranophosphophate, methyl phosphonate bindings from bindings among nucleotides, or may be modification to peptide nucleic acid (PNA) or modification to locked nucleic acid (LNA).

The ASO usable in the present invention is not specifically limited as long as it is used for therapy or research, and ASO with respect to any gene used for gene therapy or gene research or having a possibility thereof to be used for gene therapy or gene research may be adopted.

In addition, the ASO of the present invention may be used not only in a complete complementary binding (perfect match) with the desired mRNA but also in an incomplete complementary binding (mismatch) in which even though the complementary binding is not achieved in some sequences, the ASO is bound to the desired mRNA to inhibit translation of the mRNA, which is apparent to those skilled in the art.

The SAMiRNA-magnetic nanoparticle complex of the present invention may improve the delivery of the double-stranded oligo RNA into the cell, and may be used with therapeutic purpose and/or diagnostic purpose of a disease model. Preparation and properties of the SAMiRNA and the magnetic nanoparticle, and cell delivery efficiency and effects will be described in more detail in the following Examples.

In addition, the present invention provides a method of treating and/or diagnosing gene using the SAMiRNA-magnetic nanoparticle complex. Specifically, the present invention provides a method of treating and/or diagnosing diseases such as cancer, infectious diseases, and the like, including: synthesizing the double-stranded oligo RNA structure, preparing the magnetic nanoparticle in which the first hydrophobic material is coated on the surface of the magnetic material and the SAMiRNA-magnetic nanoparticle complex, administering the SAMiRNA-magnetic nanoparticle complex in the body.

The present invention provides a composition for therapy and/or diagnosis, containing the SAMiRNA-magnetic nanoparticle complex. In particular, the present invention has an advantage in that the SAMiRNA-magnetic nanoparticle complex is capable of simultaneously performing the therapy and the diagnosis. The composition of the present invention may additionally contain one or more kinds of pharmaceutically acceptable carrier in addition to the above-described effective components for administration. The pharmaceutically acceptable carrier is required to be compatible with the effective components of the present invention, and may be used by mixing one or more components selected from the group consisting of saline, sterile water, Ringer's solution, buffered saline, dextrose solution, maltodextrin solution, glycerin and ethanol, and other conventional additives such as antioxidant, buffer, fungistat, and the like, may be added thereto as needed. In addition, the composition may be prepared as a formulation for injection, such as an aqueous solution, suspension, emulsion, and the like, by additionally adding diluent, dispersant, surfactant, binder and lubricant thereto. In particular, it is preferred to provide the composition prepared as a lyophilized formulation. To prepare the lyophilized formulation, any method which is generally known in the technical field of the present invention may be used, wherein a stabilizer for lyophlization may be added thereto.

The composition of the present invention may be prepared by additionally containing one or more kinds of pharmaceutically active components in addition to the above-described effective components for administration. The pharmaceutically effective components may be one or more selected from the group consisting of anticancer agents, antibiotics, hormone, hormone antagonists, interleukin, interferon, growth factors, tumor necrosis factors, endotoxin, lymphotoxin, urokinase, streptokinase, tissue plasminogen activators, RNA degradation inhibitors, alkyl phosphocholine, radioisotope labeled component, surfactant, cardiovascular drugs, gastrointestinal drugs, and nervous system drugs.

The pharmaceutical composition of the present invention may be determined based on general symptoms of the patient and severity of the disease by general experts in the art. In addition, the composition may be formulated with various types such as powder, tablet, capsule, solution, injection, ointment, syrup, and the like, and may be provided as a unit-dosage container or multi-dosage container, for example, a sealed ampoule, bottle, and the like.

The pharmaceutical composition of the present invention may be orally or parenterally administered. Examples of an administration route of the pharmaceutical composition according to the present invention may include oral, intravenous, intramuscular, intra-arterial, intramedullary, intradural, intracardiac, transdermal, subcutaneous, intraperitoneal, intestinal, sublingual or topical administration, but the present invention is not limited thereto.

For the clinical administration as described above, the pharmaceutical composition of the present invention may be prepared as an appropriate formulation by known technology. The dosage of the composition of the present invention may have various ranges thereof depending on weight, age, gender, health condition, diet, an administration time and method, an excretion rate, the severity of disease, and the like, of a patient, and may be easily determined by a general expert in the art.

Hereinafter, the present invention will be described in detail with reference to the following Examples. These examples are only for exemplifying the present invention, and it will be obvious to those skilled in the art that the scope of the present invention is not construed to be limited to these examples.

EXAMPLE 1

Preparation of SAMiRNA-Magnetic Nanoparticle Complex

A SAMiRNA-magnetic nanoparticle complex was prepared as a complex form by preparing a double-stranded oligo RNA structure and a magnetic nanoparticle in which a first hydrophobic material is coated onto a surface of a magnetic material, respectively, and mixing the two materials.

EXAMPLE 1-1

Preparation of Double-Stranded Oligo RNA Structure

Hereinafter, in order to inhibit Survivin, a double-stranded oligo RNA to Survivin was used. The Survivin, which is protein commonly expressed in most neoplastic tumors or transformed cell lines tested until now, is expected as an important target in cancer treatment (Survivin: a new target for anti-cancer therapy. Cancer Treat Rev. 2009 November; 35(7): 553-62).

The double-stranded oligo RNA to Survivin of the present invention consists of a sense strand of SEQ ID NO: 1 and an antisense strand of a complementary sequence thereto, and a double-stranded oligo RNA used as a control group consists of a sense strand of SEQ ID NO: 2 and an antisense strand of a complementary sequence thereto. The double-stranded oligo RNA used in the present Example consists of the following base sequences.

```
                              (SEQ ID NO: 1)
5'-AAG GAG AUC AAC AUU UUC A-3'

(SEQ ID NO: 2)
5'-CUU ACG CUG AGU ACU UCG A-3'
```

In the double-stranded oligo RNA, the double-stranded oligo RNA single strand was synthesized by a method of using 2'tert-butyldimethylsilyl protected β-cyanoethylphosphoramidite to connect a phosphodiester bond forming a DNA framework. A desired sequence of the RNA is obtained by starting the synthesis process on the solid support (CPG) containing nucleoside bound thereto and repeating a cycle including deblocking, coupling, capping, and oxidation.

Specifically, the deblocking step which is a first step of the cycle is to remove DMT (4,4'-dimethoxytrityl) by treating the solid support (CPG) containing the nucleotide bound thereto with 3% trichloroacteic acid, and the coupling step which is the next to the first step is to connect the oligonucleotide chain through a coupling reaction between 5'-hydroxyl group formed in the previously formed solid support (CPG) and nucleoside phosphoramidite monomer having a desired sequence.

The capping step which is a third step is to exclude an oligonucleotide chain having a non-desired base sequence in a coupling process of a next cycle by blocking 5'-hydroxyl group which is non-reacted in the coupling step, wherein acetylation is performed by therapy of acetic anhydride and N-methylimidazole. The oxidation step which is the last step is to convert a phosphitetriester bond, which is caused by the coupling between 5'-hydroxyl group and the phosphoramidite, formed in the coupling step, into a phosphodiester bond, wherein phosphite is converted into phosphate by treatment of an 0.02 M oxidizing solution (0.02 M-I2 in THF/Pyridine/$H_2O$). A series of the corresponding RNA single strand was synthesized by an RNA 384 Synthesizer (BIONEER, Korea).

In the double-stranded oligo RNA sense strand of the double-stranded oligo RNA structure, as described above, the synthesis was performed by using β-cyanoethylphosphoramidite to connect the phosphodiester bond forming the RNA framework and polyethylene glycol (PEG) phosphoramidite was additionally connected to 5' end, thereby preparing the double-stranded oligo RNA sense strand of the double-stranded oligo RNA structure. In the antisense strand performing the annealing with the RNA-hydrophilic polymer structure sense strand, as described above, the synthesis was performed by using β-cyanoethylphosphoramidite to connect the phosphodiester bond forming the RNA framework, and $C_{24}$ tetradocosane reagent containing a disulfide bond was additionally coupled to 5' end through the general cycle including deblocking, coupling, capping, and oxidation, thereby preparing an antisense strand of an RNA-second hydrophobic polymer structure.

In the double-stranded oligo RNA structure containing the ligand bound thereto, as described above, the synthesis was performed by using β-cyanoethylphosphoramidite to connect the phosphodiester bond forming the RNA framework, polyethylene glycol (PEG) phosphoramidite was additionally coupled to 5' end, phosphoramidite containing the ligand bound thereto or an NHS typed-bindable ligand containing the ligand bound thereto was prepared, and the ligand was bound to the end portion of polyethylene glycol (PEG), thereby preparing a sense strand of an RNA-second hydrophobic polymer structure containing the ligand bound thereto. The antisense strand performing an annealing with the double-stranded oligo RNA structure containing the ligand bound thereto was prepared by the same method as that of the antisense strand of the double-stranded oligo RNA structure as described above.

When the synthesis was completed, RNA synthesized by treatment with 28% (v/v) of ammonia in hot water bath at 60° C. and RNA-polymer structures (sense strand of the RNA-hydrophilic polymer structure, antisense strand of the RNA-second hydrophobic polymer structure, sense strand of the RNA-hydrophilic polymer structure containing the ligand bound thereto) were separated from the solid support (CPG) and the protecting moiety was removed by deprotection reaction. The double-stranded oligo RNA and the double-stranded oligo RNA structure from which the protecting moiety was removed were treated with N-methylpyrolidon, triethylamine and triethylaminetrihydrofluoride with a volume ratio of 10:3:4 in an oven at 70° C. to remove 2' TEDMS (tert-butyldimethylsilyl).

RNAs in the reactants were separated by high performance liquid chromatography (HPLC) (LC-20A Prominence, SHIMADZU, Japan), and molecular weights thereof were measured by MALDI-TOF mass spectrometry (MALDI-TOF MS, SHIMADZU, Japan) to confirm whether or not a desired single strand of the RNA-polymer structure having base sequences to be synthesized corresponds to a single strand of the RNA-polymer structure containing the ligand bound thereto.

Then, in order to prepare each double-stranded oligo RNA structure, the sense strand and the antisense strand in an equivalent amount were mixed to each other and put into 1× annealing buffer (30 mM HEPES, 100 mM potassium acetate, 2 mM magnesium acetate, pH 7.0 to 7.5), followed by reaction in a constant temperature water bath at 90° C. for 3 minutes, and then reacted again at 37° C., thereby preparing the desired double-stranded oligo RNA structure and the desired double-stranded oligo RNA structure containing the ligand bound thereto, respectively. The annealings of the prepared double-stranded oligo RNA structure were confirmed by electrophoresis.

EXAMPLE 1-2

Preparation of Magnetic Nanoparticle in which First Hydrophobic Material is Coated onto Surface of Magnetic Material For the magnetic nanoparticle in which the first hydrophobic material is coated onto the surface of the magnetic material, an iron oxide nanoparticle was prepared by including: i) reacting iron chloride dissolved into water with sodium oleate dissolved into a solvent mixture containing ethanol, distilled water and nucleic acid to form an oleic acid iron complex; and ii) adding dehydrated octadecene and oleic acid mixture to the oleic acid iron complex under an inert environment and heating the complex to produce the nanoparticle, thereby completely degrading the oleic acid iron complex. The solution containing the nanoparticles produced by the reaction was cooled at room temperature, an excessive amount of ethanol was added thereto, followed by separation by centrifugation and washing process through removal of supernatant three times, and then ethanol contained in the residual was removed by vacuum drying. The reactant was easily re-dispersed into nucleic acid to prepare a desired iron nanoparticle (Korean Patent Laid-Open Publication No. 2007-0102672).

EXAMPLE 1-3

Preparation of SAMiRNA-Magnetic Nanoparticle Complex

The double-stranded oligo RNA structure and the magnetic nanoparticle in which the first hydrophobic material was coated onto the surface of the magnetic material form the SAMiRNA-magnetic nanoparticle complex containing the magnetic nanoparticle as a core by a hydrophobic interaction of the second hydrophobic material bound to one end side of the double-stranded oligo RNA structure (see FIG. 1).

The double-stranded oligo RNA structure prepared by the Example 1-1 above and the magnetic nanoparticle in which the first hydrophobic material was coated onto the surface of the magnetic material, prepared by the Example 1-2 were used to form a homogeneous SAMiRNA-magnetic nanoparticle complex by ultrasonic homogenizer. In detail, 1.5 mg of the double-stranded oligo RNA structure was dissolved into 2 ml of Dulbecco's Phosphate Buffered Saline (DPBS) and 200 µl of magnetic nanoparticle (20 nm, 1 wt %, in hexane) was added thereto. The size of the nanoparticle was homogenized (200 W, 40 kHz, on ice) by ultrasonic homogenizer (Wiseclean, DAIHAN, Korea), followed by centrifugation at 5000 rpm for 10 minutes, to collect a medium layer in which the SAMiRNA-magnetic nanoparticle complex is present.

EXAMPLE 2

Analysis of Physical Properties of SAMiRNA-Magnetic Nanoparticle Complex

Formation of the SAMiRNA-magnetic nanoparticle complex prepared by the Example 1-3 above and a shape thereof were confirmed.

EXAMPLE 2-1

Measurement of Particle Size and Polydispersity Index (PDI) of the SAMiRNA-Magnetic Nanoparticle Complex A size of the nanoparticle was measured by zeta-potential measurement. A size of the SAMiRNA-magnetic nanoparticle complex prepared by the Example 1-3 above was measured by zeta-potential measurement (Nano-ZS, MALVERN, England), wherein a refractive index of the material was 1.454, an absorption index thereof was 0.001, a temperature of water solvent was 25° C., and viscosity and refractive index thereof were correspondingly input. One-time measurement was conducted by size measurement with 20 times repeat and then this measurement was repeated three times.

Figure 2:
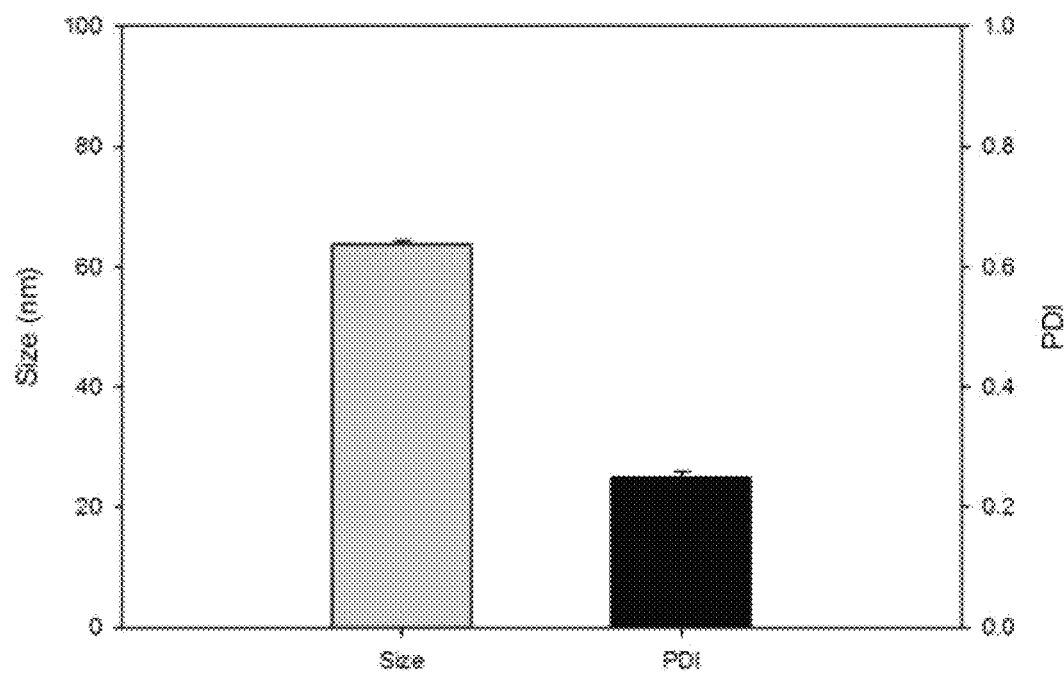
FIG. 2 is a graph showing polydispersity index (PDI) of the SAMiRNA-magnetic nanoparticle prepared by Example 1-3.

It could be confirmed that the SAMiRNA-magnetic nanoparticle complex had a size of less than 100 nm and polydispersity index (PDI) of less than 0.3 (see FIG. 2). The polydispersity index (PDI) is a value of determining that as the polydispersity index (PDI) is decreased, the corresponding particles are uniformly distributed, wherein the nanoparticles were relatively uniformly formed, which is enough to be ingested into the cells by endocytosis (Kenneth A. Dawson et al. nature nanotechnology 4:84-85, 2009). It could be confirmed that the SAMiRNA-magnetic nanoparticle complex had a structure in which the magnetic nanoparticles were positioned in the particles, the structure of the SAMiRNA-magnetic nanoparticle complex was stabilized by the interaction between the first hydrophobic material coated onto the magnetic nanoparticle and the second hydrophobic material of the double-stranded oligo RNA structure, such that the SAMiRNA-magnetic nanoparticle complex had relatively small and uniform size.

EXAMPLE 2-2

Observation of SAMiRNA-Magnetic Nanoparticle Complex By TEM

The SAMiRNA-magnetic nanoparticle complex was observed by transmission electron microscope (TEM).

Figure 3:
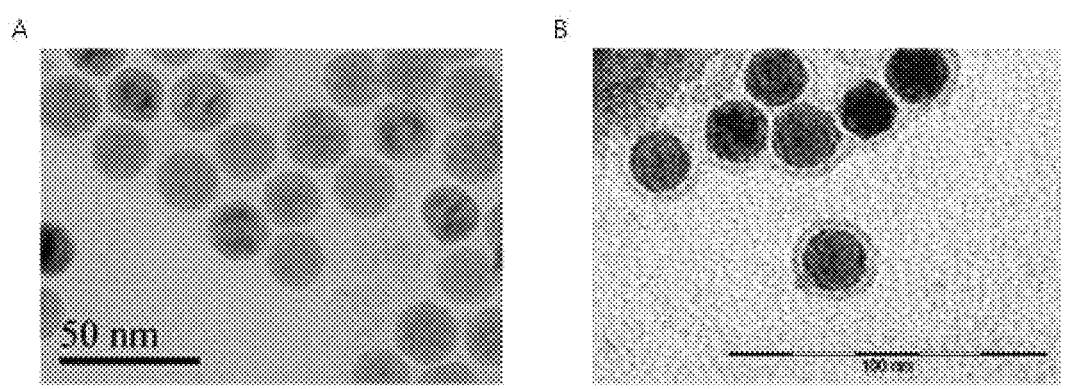
FIG. 3 is a photograph of the SAMiRNA-magnetic nanoparticle complex by Transmission Electron Microscope (TEM)

Specifically, the SAMiRNA-magnetic nanoparticle complex prepared by the Example 1-3 above was homogenized to be observed. It could be confirmed that the nanoparticles observed by TEM were well formed so that the nanoparticle had a similar size to that of the nanoparticle measured by the Example 2-1 above, and a surface consisting of the double-stranded oligo RNA structure was additionally formed on the surface of the corresponding magnetic nanoparticle, unlike the photograph obtained by observing only the magnetic nanoparticles in which the first hydrophobic material was coated onto the surface of the magnetic material (see FIG. 3).

EXAMPLE 3

Inhibition of Expression of Target Gene in Tumor Cell Line Using SAMiRNA-Magnetic Nanoparticle Complex A tumor cell line, specifically, human cervical cancer cell line (HeLa) was transformed by the SAMiRNA-magnetic nanoparticle complex prepared by the Example 1-3 above, and expression patterns of a survivin gene which is a target gene in the transformed tumor cell line were analyzed.

EXAMPLE 3-1

Culture of Tumor Cell Line

10% (v/v) fetal bovine serum, 100 units/ml of penicillin and 100 μg/ml of streptomycin were added to ATCC-formulated Eagle's minimum essential medium (EMEM culture medium) (USA) containing HeLa acquired from American type Culture Collection (ATCC) and then cultured at 37° C. and 5% (v/v) $CO_2$.

EXAMPLE 3-2

Transformation of Tumor Cell Line Using SAMiRNA-Magnetic Nanoparticle Complex

The tumor cell line ($1.3 \times 10^5$ per each well) cultured in the Example 3-1 above were cultured in a 6-well plate in the EMEM culture medium for 18 hours under the same condition as the Example 3-1 above, the medium was removed, and the equivalent amount of Opti-MEM medium per each well was deposited.

The SAMiRNA-magnetic nanoparticle complex prepared by the Example 1-3 above was added to 100 μl of Opti-MEM medium to prepare a transformation solution of the SAMiRNA-magnetic nanoparticle complex. Then, 100 to 200 nM of the transformation solution was treated to each well of the tumor cell line in which Opti-MEM was deposited and then cultured at 37° C. and 5% (v/v) $CO_2$ for total 48 hours.

EXAMPLE 3-3

Relative Quantitative Analysis of mRNA of Survivin Gene

The total RNA was extracted from the transfected cell line in the Example 3-2 above, cDNA was synthesized, and an expression amount of mRNA of Survivin was relatively quantitative analyzed by real-time PCR according to a method disclosed in Korean Patent Laid-Open Publication No. 2009-0042297.

It could be confirmed that in the Experimental group in which the SAMiRNA-magnetic nanoparticle complex containing the double-stranded oligo RNA of SEQ ID NO: 1 was treated, the expression of the mRNA of Survivin which is a target gene of the double-stranded oligo RNA contained in the corresponding nanoparticles was more inhibited as compared to a control group of the SAMiRNA-magnetic nanoparticle complex containing the double-stranded oligo RNA of SEQ ID NO: 2.

EXAMPLE 4

Magnetic Resonance Imaging (MRI) Scan of SAMiRNA-Magnetic Nanoparticle Complex

In order to confirm a diagnosis possibility of magnetic resonance imaging (MRI) under in vivo conditions of the SAMiRNA-magnetic nanoparticle complex prepared by the same method as the Example 1-3 above, a tumor consisting of KB cell line which is an oral cavity cancer epithelial cell was injected into mice, and diagnosis of cancer was confirmed by MRI scanner.

EXAMPLE 4-1

Preparation of KB Xenograft Model $1 \times 10^6$ of the KB cell line cultured in the Example 3-1 above was subcutaneously injected into both parts of the back of 5-week-old nude mice (BALB/C nu) to induce growth of the two tumor tissues. After the injection, tumor growth was observed by measuring each length of a major axis and a minor axis of the tumor every 2 days, and at the time point of 2 weeks after injection, it was confirmed that the tumor was grown as about 200 to 350 $mm^3$.

EXAMPLE 4-2

Injection of SAMiRNA-Magnetic Nanoparticle Complex and MRI Scan

Figure 4:
FIG. 4 is a magnetic resonance imaging (MRI) image of the SAMiRNA-magnetic nanoparticle complex (performed by administering the SAMiRNA-magnetic nanoparticle complex into a tumor of KB xenograft mouse model and confirming diagnosis of cancer tissue (marked by a dotted line) by MRI scanner.
Figure 4:
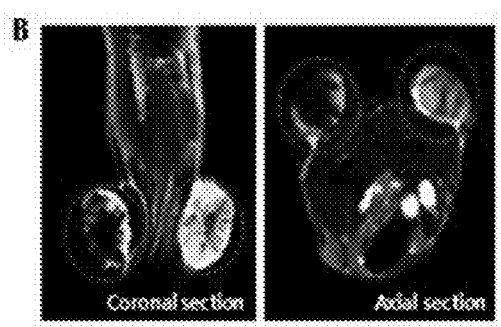

300 μg (left) and 30 μg (right) of the SAMiRNA-magnetic nanoparticle complex prepared by the same method as the Example 1-3 above were intra-tumor single-injected into both sides of cancer tissue of the KB xenograft model prepared by the Example 4-1 above, followed by MRI scan (T4.7 MRI, Bruker, Germany). In Experimental Group into which the SAMiRNA-magnetic nanoparticle complex was injected (see (B) of FIG. 4, (A) is a non-injected group), imaging signal of the cancer tissue in 300 μg injected tumor part was shown as black to confirm the presence of the cancer tissue, which has a similar degree to the imaging signal of the Experimental Group into which the magnetic nanoparticle was only injected, and thus, it could be confirmed that the cancer tissue was capable of being diagnosed by the SAMiRNA-magnetic nanoparticle complex (see FIG. 4; scanning angle—Coronal Section, coronal section Axial Section, section perpendicular to the side).

INDUSTRIAL APPLICABILITY

The SAMiRNA-magnetic nanoparticle complex according to the present invention may increase a cell delivery efficiency due to improved in vivo stability of the double-stranded oligo RNA and a homogeneous size of the nanoparticle to have excellent therapeutic efficacy, and may be utilized with a diagnosis purpose due to property of the magnetic nanoparticle. That is, the SAMiRNA-magnetic nanoparticle complex is capable of being used in a so-called theragnosis in which therapy and diagnosis are simultaneously performed, to thereby be significantly useful throughout various industrial fields such as basic research for biotechnology, pharmaceutical industry, and the like, as a new type of double-stranded oligo RNA delivery system for diagnosis and therapy of diseases.

The invention claimed is:

1. A SAMiRNA(s)-magnetic nanoparticle(s) complex comprising: magnetic nanoparticle(s) comprising first hydrophobic material coated on a surface of a magnetic material; and a structure comprising second hydrophobic material, double stranded oligo RNA and hydrophilic material wherein the structure is represented by the following Formula (1):

A-X—R—Y—B  Formula (1)

wherein: one of A and B is said hydrophilic material, the other one is said second hydrophobic material; X and Y are each independently a simple covalent bond or a linker-mediated covalent bond; and R is said double-stranded oligo RNA, and wherein the magnetic nanoparticle is positioned in a core by hydrophobic interaction between the first hydrophobic material and the second hydrophobic material, the structure is positioned in a shell, and the hydrophilic material of the structure is bound to the outermost side of the double-stranded oligo RNA.

2. The SAMiRNA-magnetic nanoparticle complex according to claim 1, wherein the first hydrophobic material and the second hydrophobic material are the same or different.

3. The SAMiRNA-magnetic nanoparticle complex according to claim 1, wherein a mass ratio of the magnetic nanoparticle to double stranded oligo RNA structure is from 0.01:1 to 100:1.

4. The SAMiRNA-magnetic nanoparticle complex according to claim 1, wherein the SAMiRNA-magnetic nanoparticle complex has a diameter of 50 to 300 nm.

5. The SAMiRNA-magnetic nanoparticle complex according to claim 1, wherein the SAMiRNA-magnetic nanoparticle complex has polydispersity index (PDI) of 0.01 to 0.4.

6. The SAMiRNA-magnetic nanoparticle complex according to claim 1, wherein the magnetic material has a diameter of 1 nm to 200 nm.

7. The SAMiRNA-magnetic nanoparticle complex according to claim 1, wherein the magnetic material is a magnetic metal or a magnetic metal oxide.

8. The SAMiRNA-magnetic nanoparticle complex according to claim 7, wherein the magnetic metal is one or more metal(s) selected from the group consisting of Fe, Ni, Co, La, Ce, Pr, Nd, Pm, Sm, Eu, Gd, Tb, Dy, Ho, Er, Tm, Yb, Lu, Cu, Ag, Au, Zn, Cd, Hg, Al, Ga, In, Tl, Ca, Sr, Ba, Ra, Pt, and Pd.

9. The SAMiRNA-magnetic nanoparticle complex according to claim 7, wherein the magnetic metal oxide is oxide of one or more metal(s) selected from the group consisting of Fe, Ni, Co, La, Ce, Pr, Nd, Pm, Sm, Eu, Gd, Tb, Dy, Ho, Er, Tm, Yb, Lu, Cu, Ag, Au, Zn, Cd, Hg, Al, Ga, In, Tl, Ca, Sr, Ba, Ra, Pt and Pd, or oxide of alloys thereof.

10. The SAMiRNA-magnetic nanoparticle complex according to claim 1, wherein the first hydrophobic material of the magnetic nanoparticle is one or more selected from the group consisting of C6 to C25 aromatic compound, C6 to C25 ether, C6 to C25 aliphatic hydrocarbon and C6 to C25 amine.

11. The SAMiRNA-magnetic nanoparticle complex according to claim 1, wherein the double-stranded oligo RNA structure has a structure represented by the following Formula (1'):

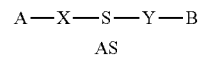

Formula (1')

Wherein A, X, Y, and B have the meanings and linkages specified in claim 1, S is a sense strand of the double-stranded oligo RNA, and AS is an antisense strand of the double-stranded oligo RNA.

12. The SAMiRNA-magnetic nanoparticle complex according to claim 1, wherein the double-stranded oligo RNA structure has a structure represented by the following Formula (2):

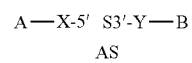

Formula (2)

Wherein A, X, Y, and B have the meanings and linkages specified in claim 1, S is a sense strand of the double-stranded oligo RNA and AS is an antisense strand of the double-stranded oligo RNA.

13. The SAMiRNA-magnetic nanoparticle complex according to claim 1, wherein the double-stranded oligo RNA has 19 to 31 nucleotides.

14. The SAMiRNA-magnetic nanoparticle complex according to claim 1, wherein the covalent bond is a non-degradable bond or a degradable bond.

15. The SAMiRNA-magnetic nanoparticle complex according to claim 14, wherein the non-degradable bond is an amide bond or a phosphate bond.

16. The SAMiRNA-magnetic nanoparticle complex according to claim 14, wherein the degradable bond is one or more selected from the group consisting of a disulfide bond, an acid degradable bond, an ester bond, an anhydride bond, a biodegradable bond and an enzymatically degradable bond.

17. The SAMiRNA-magnetic nanoparticle complex according to claim 1, wherein the second hydrophobic material has a molecular weight of 100 to 2,000.

18. The SAMiRNA-magnetic nanoparticle complex according to claim 1, wherein the second hydrophobic material is one or more selected from the group consisting of a steroid derivative, a glyceride derivative, glycerol ether, polypropylene glycol, unsaturated or saturated C12 to C50 hydrocarbons, diacylphosphatidylcholine, fatty acid, phospholipid and lipopolyamine.

19. The SAMiRNA-magnetic nanoparticle complex according to claim 18, wherein the steroid derivative is one or more selected from the group consisting of cholesterol, cholestanol, cholic acid, cholesteryl formate, cholestanyl formate, and cholestanyl amine.

20. The SAMiRNA-magnetic nanoparticle complex according to claim 18, wherein the glyceride derivative is one or more selected from the group consisting of mono-, di- and tri-glyceride.

21. The SAMiRNA-magnetic nanoparticle complex according to claim 1, wherein the hydrophilic material is a non-ionic polymer having a molecular weight of 1,000 to 10,000.

22. The SAMiRNA-magnetic nanoparticle complex according to claim 1, wherein the hydrophilic material is one or more selected from the group consisting of polyethylene glycol (PEG), polyvinylpyrolidone and polyoxazoline.

23. The SAMiRNA-magnetic nanoparticle complex according to claim 1, wherein said structure comprises a ligand bound thereto.

24. The SAMiRNA-magnetic nanoparticle complex according to claim 23, wherein the ligand is one or more, which is bound in a target-specific way to effect receptor-mediated endocytosis (RME), selected from the group consisting of target specific antibody, aptamer, peptide, and a receptor-specific chemical material.

25. The SAMiRNA-magnetic nanoparticle complex according to claim 23, wherein the receptor-specific chemical material is one or more selected from the group consisting of folate, N-acetyl galactosamine (NAG) and mannose.

26. A method of preparing SAMiRNA(s)-magnetic nanoparticle(s) complex according to claim 1, said method comprising:
  (1) preparing a double-stranded oligo RNA structure containing a hydrophilic material and a second hydrophobic material bound thereto;
  (2) preparing a magnetic nanoparticle comprising a first hydrophobic material coated on a surface of the magnetic material; and
  (3) mixing a SAMiRNA comprising the double-stranded oligo RNA structure and the magnetic nanoparticle containing the first hydrophobic material coated on the surface of the magnetic material.

27. The method according to claim 26, wherein the method further comprises a step of binding a ligand to the hydrophilic material of the double-stranded oligo RNA structure.

28. A pharmaceutical composition comprising a SAMiRNA magnetic nanoparticle complex according to claim 1.

29. A composition for diagnosis comprising a SAMiRNA-magnetic nanoparticle complex according to claim 1.

30. A composition for performing diagnosis and treatment simultaneously, comprising a SAMiRNA-magnetic nanoparticle complex according to claim 1.

* * * * *

UNITED STATES PATENT AND TRADEMARK OFFICE
CERTIFICATE OF CORRECTION

| | |
|---|---|
| PATENT NO. | : 9,649,388 B2 |
| APPLICATION NO. | : 14/372211 |
| DATED | : May 16, 2017 |
| INVENTOR(S) | : Jeiwook Chae et al. |

It is certified that error appears in the above-identified patent and that said Letters Patent is hereby corrected as shown below:

In the Specification

Column 5, Line 54: "La, Ce, Pr, Nd, Pm, Sm, Gd, Tb" should be --La, Ce, Pr, Nd, Pm, Sm, Eu, Gd, Tb--.

In the Claims

Column 22, Line 59: "diand tri-glyceride" should be --di-, and tri-glyceride--.

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*